United States Patent [19]

Klein et al.

[11] Patent Number: 4,843,154
[45] Date of Patent: Jun. 27, 1989

[54] ISOMALTAMINES AND THEIR N-ACYL DERIVATIVES, METHODS FOR THEIR PRODUCTION, AND THEIR USES AS SURFACTANTS AND MONOMERS

[75] Inventors: Joachim Klein, Braunschweig; Wolfgang Behrens, Wolfsburg; Markwart Kunz, Braunschweig, all of Fed. Rep. of Germany

[73] Assignee: Sueddeutsche Zucker-Aktiengesellschaft, Mannheim, Fed. Rep. of Germany

[21] Appl. No.: 80,266

[22] Filed: Jul. 31, 1987

[30] Foreign Application Priority Data

Jul. 31, 1986 [DE] Fed. Rep. of Germany ....... 3625931

[51] Int. Cl.$^4$ ...................... C07H 15/04; C08F 20/36; C08F 22/22; B01F 17/56
[52] U.S. Cl. ................................. 536/4.1; 252/174.7; 252/174.18; 252/357; 252/546; 252/548; 536/17.9; 536/126
[58] Field of Search ................ 536/4.1, 17.9; 252/546, 252/548

[56] References Cited

U.S. PATENT DOCUMENTS

| | | | |
|---|---|---|---|
| 2,016,962 | 10/1935 | Flint et al. | 536/553 |
| 2,830,983 | 4/1958 | Lemieux | 564/472 |
| 4,486,418 | 12/1984 | Watanabe et al. | 536/16.8 |
| 4,563,445 | 9/1986 | Feizi et al. | 536/17.2 |
| 4,618,675 | 10/1986 | Lichtenthaler et al. | 536/4.1 |
| 4,631,272 | 12/1986 | Lockhoff et al. | 536/22 |

FOREIGN PATENT DOCUMENTS

0096392 10/1985 European Pat. Off. .
220676 5/1987 European Pat. Off. .

OTHER PUBLICATIONS

"Chemistry and Technology of Water–Soluble Polymers", C. A. Finch, Plenum Press, New York, 1983, p. 11 ff.
J. Klein, D. Herzog, Macromol. Chem. Rap. Comm. 1986.

Primary Examiner—A. Lionel Clingman
Attorney, Agent, or Firm—Armstrong, Nikaido, Marmelstein, Kubovcik & Murray

[57] ABSTRACT

According to the present invention, in the first instance, new aminopolyols, which can be obtained from the disaccharides isomaltose, isomaltulose and α-D-glucopyranosyl (1→1)-D-fructose, are prepared. These compounds, designated as isomaltamines and having the formulae:

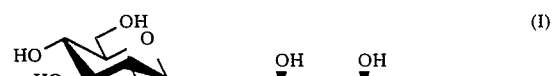

(I)

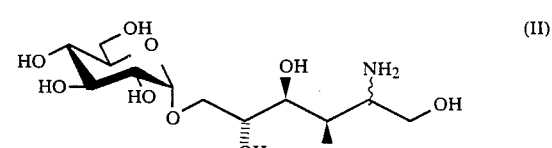

(II)

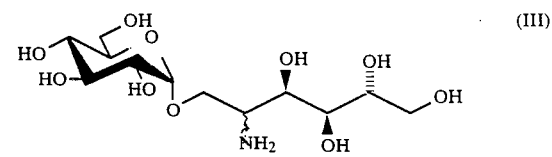

(III)

as well as mixtures of the same, are produced by the reductive amination of the aforementioned saccharides by means of ammonia or hydrazine compounds in the presence of catalysts, such as Raney nickel, and hydrogen, or by means of complex metallic hydrides, such as sodium borohydride, in solution or suspension. The invention relates, furthermore, to the N-acyl derivatives of the individual isomaltamines or their mixtures as well as to the production of the N-acylates by a selective N-acylation. Depending upon the nature of the acyl radical, these acylates can be used for example, as surfactants or (similarly to N-acrylamide) for the production of polymers.

7 Claims, No Drawings

ISOMALTAMINES AND THEIR N-ACYL DERIVATIVES, METHODS FOR THEIR PRODUCTION, AND THEIR USES AS SURFACTANTS AND MONOMERS

BACKGROUND OF THE INVENTION

This invention relates to isomaltamines and their N-acyl derivatives, to methods for their production, and to their uses.

Aminopolyols, as well as methods for the production of aminopolyols by reducing carbohydrates, are known from U.S. Pat. Nos. 2,016,962 and 2,830,983 and German Democratic Republic Patent Specification No. 13746.

SUMMARY OF THE INVENTION

According to the present invention, there are provided isomaltamines having the formulae (I) to (III):

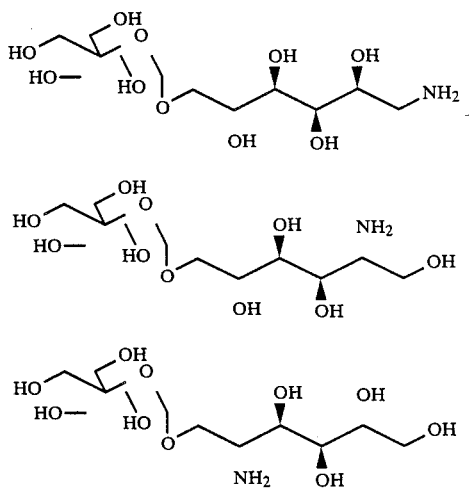

and the isomers thereof, and mixtures thereof in any ratio.

The present invention also provides N-acyl isomaltamines derivatives having the formulae (IV) to (VI).

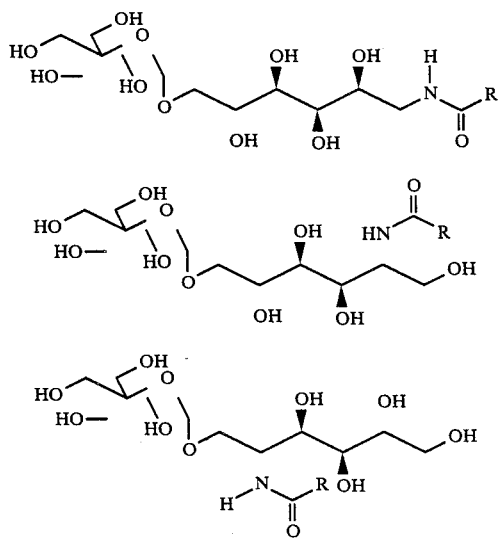

wherein R is a branched or unbranched, saturated or unsaturated, alkyl radical having at least 2 carbon atoms, and the isomers thereof, and mixtures thereof in any ratio.

The invention also provides a method for producing an isomaltamine of formula (I), (II) or (III) above, which comprises the steps of:

(a) subjecting a compound selected from the group consisting of isomaltose, isomaltulose and α-D-glucopyranosyl-(1→1)-D-fructose to reductive amination by means of a compound selected from ammonia, hydrazine and hydrazine derivatives, either (i) in the presence of a catalyst and hydrogen, or (ii) by means of a complex metallic hydride, in an aqueous, aqueous-alcoholic or alcoholic solution or suspension; and (b) subjecting the resulting product to isolation and/or purification by means of an acid cationic exchanger.

Preferably the catalyst is Raney nickel. Preferably the complex metallic hydride is sodium borohydride. The isolation is preferably effected by fractional precipitation by means of a solvent, e.g. methanol, acetone or ether.

The present invention further provides a method for producing an N-acyl isomaltamine derivative of formula (IV), (V) or (VI) above, which comprises the steps of:

(a) subjecting an isomaltamine derivative selected from the group consisting of those having the formulae (I) to (III) as given above, and mixtures thereof in any ratio, to selective N-acylation by the use of a compound selected from the group consisting of acid halides and acid anhydrides in an aqueous, aqueous-alcoholic or alcoholic solution or suspension; and (b) subjecting the resulting product to isolation and purification by precipitation and/or by crystallization and/or by extraction.

Preferably step (a) is carried out in the presence of a basic substance, e.g. a substance selected from the group consisting of potassium carbonate, sodium carbonate and basic ion exchangers.

DESCRIPTION OF THE PREFERRED EMBODIMENTS

The isomaltamines of the formula (I) to (III) are produced from the disaccharides isomaltose, isomaltulose and α-D-glucopyranosyl(1→1)-D-fructose, also called trehalulose herein.

The production of the isomaltamines according to the invention having the formula (I) to (III) can be effected in accordance with methods mentioned in the literature, starting from isomaltose, isomaltulose and trehalulose, by the use of various amination agents (such as ammonia, hydrazine or hydrazine derivatives) in various solvents (e.g. water, methanol or mixtures of water and methanol) by the use of various reducing methods either catalytically (e.g. in the presence of copper, platinum or palladium catalysts, preferably a Raney nickel catalyst, and hydrogen) or with complex metallic hydrides (such as sodium borohydride).

The names of the isomers according to the invention having formulae (I), (II) and (III) are:

Formula (I)

α-D-1-desoxy-1-amino-glucopyranosyl-(1'→6)-D-sorbitol[1-amino-(1'→6)-GPS or 1'→6-isomaltamine-(1) are recommended as abbreviated names]

Formula (II)

α-D-2-desoxy-2-amino-glucopyranosyl-(1'→6)-D-sorbitol[abbreviated as 2-amino-(1'→6)-GPS] or α-D-2-desoxy-2-amino-glucopyranosyl-(1'→6)-D-mannitol-[abbreviated as 2-amino-(1'→6)-GPM] for the isomers; a mixture of the two isomers (according to formula (II)) could be designated, in accordance with the generic name (isomalt) for the hydrogenation product of isomaltulose, as 2-desoxy-2-amino-(4→6)-isomalt[or, for short, (1'→6)-isomaltamine-(2))]

Formula (III)

α-D-2-desoxy-2-amino-glucopyranyosyl-(1'→1)-D-sorbitol [abbreviated as 2-amino-(1'→1)-GPS] or α-D-2-desoxy-2-amino-glucopyranosyl-(1'→1)-D-mannitol [abbreviated as 2-amino-(1'→1)-GPM] for the isomers; a mixture of the two isomers could be designed as 2-desoxy-2-amino-(1'→1)-isomalt [or, for short, (1'→1)-isomaltamine-(2)].

The structure of the aforementioned amines can be determined by NMR spectra.

The isomers differ, in the same way as mannitol and sorbitol or glucopyranosyl-(1'→6)-mannitol and glucopyranosyl-(1'→6)-sorbitol, essentially in the terms of their solubility. For example, 1- and 2-amino-(1'→6)-GPS are readily soluble in water-free methanol, whilst 2-amino-(1'→6) GPM precipitates upon the addition of methanol to concentrated aqueous solutions. The isomers according to formula (III) demonstrate corresponding dissolving behaviour.

Isomaltulose, as one of the educts for the preparation of aminopolyols according to the invention, can be prepared by enzymatic transglucosidation, e.g. on a large scale, in an extremely pure crystalline form (see H. Schiweck, Ullmann's Encyclopädie der Technischen Chemie, 4th Edition, Vol. 24, p. 780 ff). On the other hand, for example, commercially available maltose contains a proportion of glucose and higher maltooligomers, to a lesser or greater extent. Trehalulose can also be prepared by the enzymatic transglucosidation of saccharose (H. Schiweck, as above).

It has surprisingly been discovered in the production and processing of the aminopolyols according to the invention that they can be separated from neutral products in a problem-free manner without decomposition, by the use of acid ion exchangers, whilst other aminopolyols, such as maltamine, when subjected to the same treatment, are partially decomposed to give glucamine and other products. Not only chemical stability, but also microbiological stability, is desired for many applications, more particularly in the case of technical auxiliary substances, e.g. in the tertiary production of petroleum. In an investigation for biological degradability, the aminopolyols according to the invention showed a surprisingly high microbiological stability.

The reductive amination with hydrazine and Raney nickel as catalyst of monosaccharides has proved good as a particularly careful method for the production of the aminopolyols, which are consequently coloured very little by the monosaccharides. Nevertheless, discolouration and decomposition cannot be completely avoided, more particularly in the case of oligosaccharides having an α-glycoside bond, such as maltose.

By way of contrast, the aminopolyols prepared according to the invention, corresponding to the formulae (I), (II) and (III), are, surprisingly, not coloured and are so stable that they can even be purified with strongly acidic cationic exchangers.

In a few applications, uniformity of the products need not be imperative. Mixtures of the aminopolyols according to the invention can be obtained in a problem-free manner from intermediate and end products of the production of palatinose. Depending upon the composition of the intermediate or end product, the aminopolyol mixtures consist of different proportions of the compounds according to formulae (I) to (III).

N-derivatives of carbohydrates meets with increasing interest in a series of applications. Thus there are, particularly in medicine, examples of pharmacologically active N-derivatives of carbohydrates (e.g. German Offenlegungsschrift No. 3405841 and European Pat. No. 0096392). N-Derivatives of aminopolyols are used overidingly in cosmetics on account of their moisture-stabilizing properties or their surfactant action (e.g. German Offenlegungsschriften Nos. 2533101 and 1261861 and Japanese Patent Publication No. 59/212419). The aminopolyols according to the invention and their derivatives likewise have, in part, moisture-stabilizing or surface-active properties. They are particularly suitable for preparing hydrophilic or amphiphilic N-acyl derivatives according to formulae (IV), (V) and (VI). These N-acylates, if the acyl moiety contains functional groups and/or double bonds, can be suitable as intermediate products or, for example if the acyl moiety contains a long-chain alkyl group, as end products.

Surprisingly, N-acrylates prepared from the aminopolyols according to the invention, and N-methacrylates, can, for example, be crystallized in a problem-free manner even if mixtures of the isomers, e.g. corresponding to formula (II), are used. On the other hand, comparable N-acrylates prepared from maltamine could not be crystallized hitherto. Depending upon the nature of the acyl radical, the derivatives are suitable, for example, as surfactants or for the production of polymers.

N-acylates according to formulae (IV), (V) and (VI) having alkyl radicals with from 5 to 21 carbon atoms are distinctly amphiphilic. Their HLB values are calculated to be between approximately 10 and approximately 15. Amphiphiles with these HLB values are used as wetting agents and as "oil in water emulsifiers" and as washing-active substances (Das Atlas-HLB-System, Atlas Chemie GmbH, Essen, 1968).

The amides according to the invention are superior to comparable amphiphiles, e.g. saccharose monoesters, on account of their higher stability with regard to both the glycosidic bond and the amide bond, vis-a-vis the ester bond. Also pure saccharose higher monoesters, for example, can only be separated from higher esterified products at great expense, whilst the amides according to the invention are pure monoderivatives (for details of saccharose esters, see G. Schuster, "Emulgatoren für Lebensmittel", Springer-Verlag, Berlin, Heidelberg N.Y., 1985, p. 142 ff.).

Water-soluble and hydrophilic polymers have many uses. They are used as thickening agents in technology, in the pharmaceutical and foodstuffs industries, for the tertiary production of petroleum and also as auxiliary agents for textile and paper production (see for example "Chemistry and Technology of Water-Soluble Polymers" edited by C. A. Finch, Plenum Press, New York 1983, p. 11 ff).

Polyvinylsaccharides of high molecular weight can be prepared from aminopolyol-N-acrylates and N-methacrylates with the corresponding purity of the derivatives (J. Klein, D. Herzog, publication being prepared, Macromol. Chem. Rap. Comm. 1986). On account of the difficulty of the isolation of pure non-coloured aminopolyols from reducing oligosaccharides such as maltamine, hitherto no aminopolyol acrylamides of high molecular weight could be obtained from oligosaccharides.

N-acylates according to the invention, prepared from acrylic acid, methacrylic acid, itaconic acid or maleic acid are obtained in particular pure form, free from disturbing accompanying brown substances, so that they are suitable, in an outstanding way, for the preparation of homopolymers and copolymers of high molecular weight.

These polymers surprisingly display a high microbiological stability in biological degradation tests, unlike many natural polysaccharides.

These polymers surprisingly display a high microbiological stability in biological degradation tests, unlike many natural polysaccharides.

Polymers prepared from the amides according to the invention by homopolymerization or copolymerization are therefore superior to other microbiologically or chemically less stable hydrophilic polymers in many applications, more particularly for the tertiary production of petroleum.

The following Examples 1 to 5 describe the production and processing of compounds according to formulae (I) to (III) from isomaltose, isomaltulose or trehalulose, and the following Examples 7 to 9 describe preparation of N-acyl aminopolyols.

EXAMPLE 1

Catalytic reductive amination of disaccharides with hydrazine 150 g of isomaltose or isomaltulose or trehalulose were dissolved at room temperature in approximately 400 ml of water, and the mixture was stirred, after the addition of approximately 50 ml of 80% hydrazine hydrate, for 6 to 12 hours at room temperature. The solution thus obtained was hydrogenated in a high-pressure autoclave in the presence of 20 g of moist Raney nickel at approximately 100 to 150 bar hydrogen pressure and at a temperature of approximately 50° C. Good stirring and tempering were important. After 6 to 18 hours, the reaction mixture was withdrawn from the autoclave and the hydrogenation catalyst was filtered off. Dissolved nickel could be removed with suitable reagents, such as diacetyldioxime, by precipitation and filtration. The removal of the nickel with a selective, organic metal extraction oil in an emulsion and subsequent phase separation is recommended for the preparation of a product of technical grade.

In an analogous manner, hydrogenation could be carried out with other catalysts, e.g. catalysts based on copper, palladium or platinum. The yields of aminosaccharide were, however, clearly less ($<20\%$), and processing by means of ion exchangers (see below) was imperative.

Depending upon the intended purpose of the aminopolyols, processing can be carried out according to two methods as follows:

(1) Purification by means of ion exchangers

The solutions of the crude products contain, in general, low proportions of non-converted educts as well as hydrogenated polyols. These can, in case a high product purity is desired, be removed by an ion exchange treatment. To this purpose, the clear filtrate of the solution freed from the catalyst is concentrated to dryness. The residue (approximately 140 g), after dissolving in a little water, is added to a cationic exchange column (e.g. 2.3 liters of IR 120 Amberlite, ($H^+$-form)), the column is washed free of sugar with approximately 10 liters of water, and is eluted with a five-fold volume of a 5% aqueous ammonia solution. The aminopolyol is obtained from the eluate by distillation to dryness (yield approximately 85%).

(2) Processing by precipitation

A clear filtrate of the solution, freed from the catalyst, of a solution of the mixture purified of polyol by ion exchange corresponding to formula (II) or (III), is concentrated to an oily consistency on a rotation evaporator in vacuum at approximately 40° to 50° C. and methanol is added to the oil whilst heat is still being applied. In the case of the preparation of the compounds according to formula (II) or (III), there precipitates, upon cooling, a mixture of the compounds in which the respective mannitol isomers predominate. By the successive addition of acetone, a second batch, consisting predominantly of the sorbitol isomers, is obtained. The precipitation is completed with ether. In the case of the preparation of the compound according to formula (I), after the methanol addition, in the first instance acetone is added to the solution until it becomes turbid and then at approximately 4° C. a mixture of acetone/ether is added until the precipitation of the reaction product is as complete as possible.

It is to be noted that, in the case of the preparation of compounds according to formula (III), the mannitol isomers may predominate in the reaction mixture after the reductive amination.

EXAMPLE 2

Catalytic reductive amination of isomaltulose with ammonia in methanol

In a pressure vessel, a suspension consisting of methanol (300 ml) saturated with ammonia at 0°, 20 g of isomaltulose, approximately 50 ml of molecular sieves (3A°) and 0.56 g of $NH_4Cl$ was stirred for 6 days at room temperature. In this time the isomaltulose dissolved completely. After the reaction, the molecular sieves were filtered off and the solution was hydrogenated in an autoclave with methanolic Raney nickel at 50° C. and approximately 120 bar hydrogen pressure for 12 hours. After the catalyst had been filtered off, a first product fraction slowly precipitated, containing mainly the mannitol isomers. Further purification and processing were carried out as described in Example 1. The yield was 7.2 g (36% of the theoretical yield).

EXAMPLE 3

Reductive amination of isomaltulose with a complex metallic hydride 40 ml of a solution obtained as in Example 2 was, after stirring for 6 days, distilled to dryness and the residue was added to an aqueous solution of sodium borohydride (0.4 g). After stirring for approximately 16 hours at room temperature, the solution was adjusted with hydrochloric acid to pH 6 and distilled to dryness. The residue was concentrated several times, after methanol has been added, to dryness until all of the borate had been removed. Purification of the borate-free residue was effected with a cationic exchanger, as described in Example 1. The yield was 1.3 g (52% of the theoretical yield).

EXAMPLE 4

Preparation of 2-amino-(1'→6) GPS from isomaltulose by Heyns rearrangement

In accordance with the preparation of glucosamine from fructose (K. Heyns; H. Paulsen; R. Eichstädt and M. Rolle, Chem. Berichte, 90 (1957) 2039) 2-amino(1' 6)-GPS was prepared from isomaltulose by way of isomaltamine (which was not isolated as an intermediate product, but was hydrogenated directly).

A suspension of 5 g isomaltulose, as described in Example 2, was stirred in the presence of molecular sieves and ammonium chloride in ammonical methanol for 6 days at room temperature. The solution obtained was concentrated, after filtering off the molecular sieves, to dryness and the residue, together with 3.5 g of succinic acid, was taken up anew in 100 ml of abs. methanol. The suspension was stirred for 4 days at 4° C. and then filtered, and the clear filtrate was concentrated to dryness. The crude product was dissolved in distilled water, stirred overnight at room temperature and the solution was then added to a cationic exchange column (e.g. IR 120 Amberlite ($H^+$-form), 200 ml).

The column was washed free of sugar with approximately 1 liter of water and was subsequently eluted with 1 liter of 0.5N trifluoroacetic acid. The eluate was substantially freed from trifluoroacetic acid with ether by means of extraction, and concentrated to dryness (1.6 g crude product). The crude product was dissolved in a little water and adjusted with aqueous ammonia to a pH of approximately 8, and 0.25 g of sodium borohydride was added to this solution. The reaction product was processed as described in Example 3. The yield was 300 mg (approximately 6%).

A chromatographic test confirmed that 2-aminio-(1'→6)-GPS had formed (for the analytical conditions, see Example 6).

EXAMPLE 5

Preparation of an aminopolyol mixture from palatinose molasses

When obtaining palatinose by crystallization, palitinose molasses were formed as a final product. These molasses were, as described in German Offenlugungsschrift No. 3241788, free of glucose, fructose and saccharose by fermentation. The yeast was separated. The solution thus obtained was aminated in a reductive manner, after decolourization by means of a decolourizing resin and/or activated carbon, in accordance with Example 1. After repeated decolourization by means of activated carbon, the solution thus obtained was, as described in Example 1, processed by means of ion exchange or by precipitation with methanol. The resulting aminopolyol mixture contained, as a chromatographic test (see Example 6) showed, aminopolyols corresponding to formulae (I) to (III).

EXAMPLE 6

The identity of the aminopolyols which were obtained by means of the various methods and which have formulae (I) to (III) was established by high-pressure fluid chromatography (ion pair chromatography) under the following conditions:

Column: RP 18 cartridge, Merck, 250-4, 7 microns
Mob.phase: approximately 2 g of ammonium heptane sulphonate/liter of water
Temperature: 20° C.
Flow: 0.7 $cm^3$/min.
Detector: differential refractometer.

After approximately 21 minutes of chromatography, a peak is formed in the chromatogram, corresponding to the released ammonium. The aminopolyols follow, timewise, after this peak in the following sequence:

2-amino-1'→1-GPS
2-amino-1'→1-GPM
2-amino-1'→6-GPS
1-amino-1'→6-GPS
2-amino-1'→6-GPM.

The chromatography conditions are applicable to a preparatory high-pressure chromatography column for the separation of the isomers from the mixtures. For the purposes of obtaining pure compounds according to formulae (II) and (III), the ion pair reagent is then removed with an anion exchanger (e.g. IRA 400 Amberlite (OH-form)). By concentration to dryness, pure compounds were obtained.

EXAMPLE 7

Selective N-acylation in aqueous solution with a short-chain acid chloride 53 g of aminopolyol corresponding to formula (I), (II) or (III) (0.16 mol) were dissolved in water with 21.3 g (0.16 mol) of potassium carbonate and 0.7 g of sodium nitrite. Acrylic acid chloride was added with vigorous stirring and cooling (maximum temperature= 5° C.), and subsequently further stirring was carried out for 1 hour at 5° C. and thereafter for a futher 10 to 15 hours at room temperature.

After precipitation with approximately 1 liter of ethanol, the inorganic salts were filtered off. A mixture of acetone/ether was added, gradually, to the clear filtrate, in the first instance at room temperature until the solution became turbid, and then at 4° C., until the reaction product had precipitated as fully as possible.

Isomer-free products were obtained by crystallization. For example if a mixture consisting predominantly of 2-amino-(1'→6)-GPS (see Example 1) was used, then, after the precipitated product had been dissolved in a little 50% methanol and after the gradual addition of ethanol, acetone and ether, the sorbitol isomer was obtained as needle-shaped crystals (yield approximately 60%).

EXAMPLE 8

Selective N-acylation with a short-chain branched acid anhydride in methanol 66.6 g (0.2 mol) of aminopolyol corresponding to formula (I), (II) or (III), prepared according to Example 1, were suspended or dissolved in 200 ml of abs. methanol. The solution was cooled to —5° C. and, whilst keeping the temperature constant, 32 g (0.2 mol) of methacrylic acid anhydride was slowly added thereto. Subsequently, it was stirred further for 18 hours at 0° C.

By addition of acetone/ether, the reaction product was precipitated. The amide, obtained in powder form, was absorbed in a little water and crystallized with ethanol/acetone/ether analogously to Example 7 (yield approximately 70%).

EXAMPLE 9

Selective N-acylation with a long-chain acid anhydride in methanol in the presence of a basic ion exchanger 3 g of aminopolyol corresponding to formula (I), (II) or (III), prepared according to Example 1, were suspended, together with 25 ml of basic ion exhanger washed with water and methanol (e.g. IRA 400 Amberlite (OH-form)) and 4.3 g of palmitic acid anhydride, in 100 ml of abs. methanol, and stirred at room temperature for 48 hours. After distilling off the methanol the residue was extracted in a Soxhlet apparatus with petroleum ether. The residue thus obtained was extracted with hot butanol and filtered. The filtrate was shaken three times with a 5% aqueous common salt solution and dried with magnesium sulphate. The residue obtained by distillation was substantially pure aminopolyol-N-acylate, as determined by thin-layer chromatography. Traces of free fatty acid possibly still appearing in the IR-spectrum could be removed by short repeated extraction with petroleum ether. The yield was approximately 50 to 60% of the theoretical yield.

EXAMPLE 10

Biological degradation test of the compounds according to the invention

The biological degradability was investigated according to DEV H5/Teil 2 (German Unit Process for water, waste water and sludge investigation)/(Part 2), using the following compounds:

1'→6-isomaltamine-(2)
1'→6-isomaltamine-(2)-N-palmitate
1'→6-isomaltamine-(2)-N-acrylate-polymer.

The biological oxygen requirement was measured in the case of, respectively, two dilutions. The oxygen consumption was not determined.

EXAMPLE 11

Preparation of an aminopolyol-N-acryl-polymer 3 g of 1'→6-isomaltamine-(2)-N-acrylamide were dissolved in 10 ml of degassed twice-distilled water and 1 drop of glacial acetic acid was added. The solution was prepared in a reaction vessel which had been gassed with highly purified nitrogen and which was thermostated. Then, 46 mg of $(NH_4)_2S_2O_8$ as an oxidising agent and 11 mg of $Na_2S_2O_5$ as a reducing agent were dissolved separately in, in each case, a few drops of degassed twice-distilled water, and injected successively into the reaction vessel through a septum. Polymerization took place at 4° C. within 3 to 6 hours. In the case of yields of 30 to 60%, molecular weights in the range of $10^5$ to $10^6$ were achieved.

We claim:

1. Isomaltamines having the formulae (I) to (III):

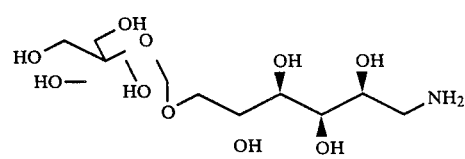

(I)

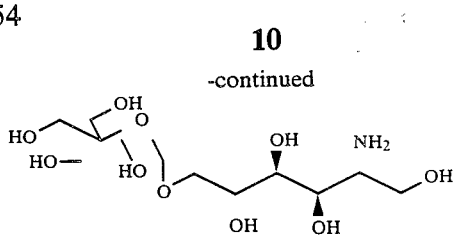

(II)

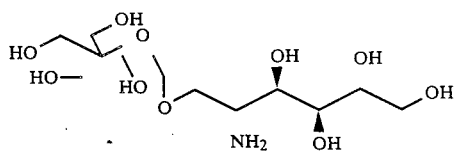

(III)

and the isomers thereof, and mixtures thereof in any ratio.

2. N-Acyl isomaltamines derivatives having the formulae (IV) to (VI):

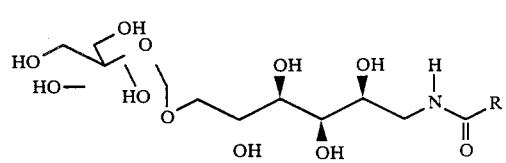

(IV)

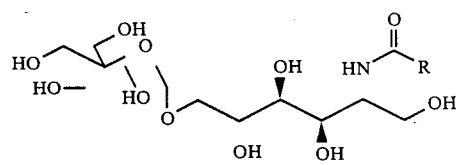

(V)

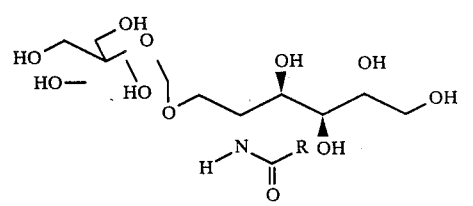

(VI)

wherein R is a branched or unbranched, saturated or unsaturated, alkyl radical having a least 2 carbon atoms, and the isomers thereof, and mixtures thereof in any ratio.

3. An isomaltamine of the formula:

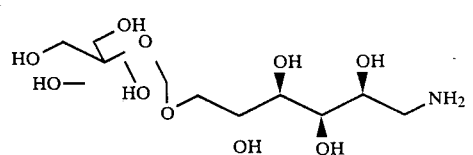

(I)

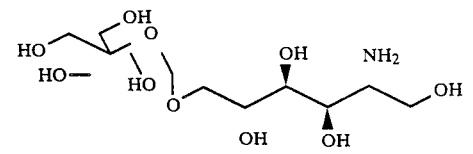

(II)

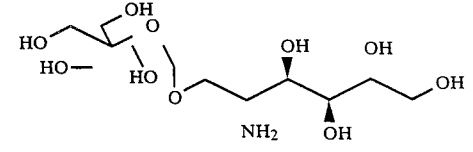

(III)

and mixtures thereof.

4. An N-acyl isomaltamine of the formula:

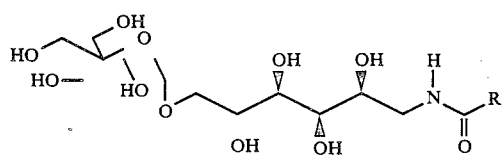
(IV)

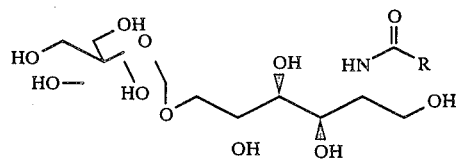
(V)

-continued

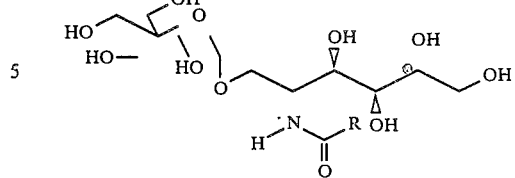
(VI)

wherein R is a branched or unbranched alkyl or alkylene group having at least 2 carbon atoms,

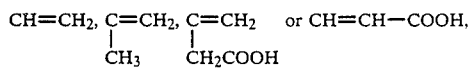

and mixtures thereof.

5. A surfactant composition comprising a compound of claim 4 wherein R is an alkyl group having 2–21 carbon atoms.

6. A wetting agent, emulsifier or a detergent composition comprising a compound of claim 4 wherein R is an alkyl group having 2–21 carbon atoms.

7. A polymerizable composition comprising a compound of claim 4 wherein R is

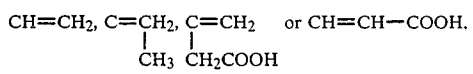

and mixtures thereof.

* * * * *